US00PP32568P2

(12) United States Plant Patent
Holtmaat

(10) Patent No.: US PP32,568 P2
(45) Date of Patent: Dec. 1, 2020

(54) ***RUDBECKIA* PLANT NAMED 'RUDBR159'**

(50) Latin Name: *Rudbeckia hirta*
Varietal Denomination: RUDBR159

(71) Applicant: Henricus Maria Joseph Holtmaat, Zuidwolde (NL)

(72) Inventor: Henricus Maria Joseph Holtmaat, Zuidwolde (NL)

(73) Assignee: NOVA PERENNE BV, Zuidwolde (NL)

( * ) Notice: Subject to any disclaimer, the term of this patent is extended or adjusted under 35 U.S.C. 154(b) by 0 days.

(21) Appl. No.: 16/873,139

(22) Filed: Feb. 7, 2020

(51) Int. Cl.
*A01H 5/02* (2018.01)
*A01H 6/14* (2018.01)

(52) U.S. Cl.
USPC ..... Plt./474

(58) Field of Classification Search
USPC ..... Plt./474
See application file for complete search history.

*Primary Examiner* — Susan McCormick Ewoldt
(74) *Attorney, Agent, or Firm* — Penny J. Aguirre

(57) ABSTRACT

A new cultivar of *Rudbeckia* plant named 'RUDBR159' that is characterized by its well-branched plant habit, its strong stems, its very floriferous blooming habit, its long flowering period, its long flowering period, and its inflorescences with ray florets that are yellow-orange in color and dark greyed-orange at the base.

2 Drawing Sheets

Botanical classification: *Rudbeckia hirta.*
Variety denomination: 'RUDBR159'.

CROSS-REFERENCE TO A RELATED APPLICATION

This application is related to a European plant breeders' rights application filed on Sep. 3, 2018, application No. 2018/2253. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Rudbeckia hirta* and will hereafter by referred to by its cultivar name, 'RUDBR159'. The new cultivar is an herbaceous perennial grown for use as a landscape plant.

'RUDBR159' was derived from a breeding program in July of 2016 conducted by the Inventor at a nursery in Zuidwolde, The Netherlands. The objective of the breeding program was to select new cultivars of *Rudbeckia* with floriferous blooming habits and compact plant habits.

'RUDBR159' was selected in July of 2017 by the Inventor from amongst seedlings in a trial field that had been planted with seed derived from open pollination of numerous unpatented and unnamed proprietary plants from the Inventor's breeding program. The exact parentage is therefore unknown.

Asexual propagation of the new cultivar was first accomplished under the direction of the Inventor by tissue culture using meristematic tissue in Heerhugowaard, The Netherlands in January 2018. Asexual propagation by tissue culture has determined that the characteristics of the new cultivar are stable and are reproduced true to type in successive generations.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure from and/or sales prior to the filing date but less. than one year prior to the effective filing date. Disclosure includes but may not be limited to a website listing by AB-Cultivars (a company owned by the Inventor).

SUMMARY OF THE INVENTION

The following traits have been repeatedly observed and represent the characteristics of the new cultivar. These attributes in combination distinguish 'RUDBR159' as a unique cultivar of *Rudbeckia.*

1. 'RUDBR159' exhibits a short plant height.
2. 'RUDBR159' exhibits a well-branched plant habit.
3. 'RUDBR159' exhibits strong stems.
4. 'RUDBR159' exhibits a very floriferous blooming habit.
5. 'RUDBR159' exhibits a long flowering period.
6. 'RUDBR159' exhibits inflorescences with ray florets that are yellow-orange in color and dark greyed-orange at the base.

'RUDBR159' can be compared to the *Rudbeckia* cultivars 'Kissing SmileyZ' (not patented), and 'Laughing SmileyZ' (not patented). 'Kissing SmileyZ' and 'Laughing SmileyZ' are both similar to 'RUDBR159' in having floriferous blooming habits. 'Kissing SmileyZ' differs from 'RUDBR159' in having a slightly taller plant height, in commencing bloom earlier in the season, and I having ray florets that are grey-orange-brown with yellow tips on the upper ¼. 'Laughing SmileyZ' differs from 'RUDBR159' in having inflorescences that are slightly larger in size, inflorescence disks that are smaller in diameter and ray florets that are clear grey-orange on the lower half and dark yellow-orange on the upper half.

BRIEF DESCRIPTION OF THE DRAWINGS

The accompanying colored photographs illustrate the overall appearance and distinct characteristics of the new *Rudbeckia*. The photographs were taken of a 4-month-old plant of 'RUDBR159' as grown outdoors in a 19-cm container in Zuidwolde, The Netherlands.

The photograph in FIG. 1 is a side view of 'RUDBR159' in bloom.

Figure 1:
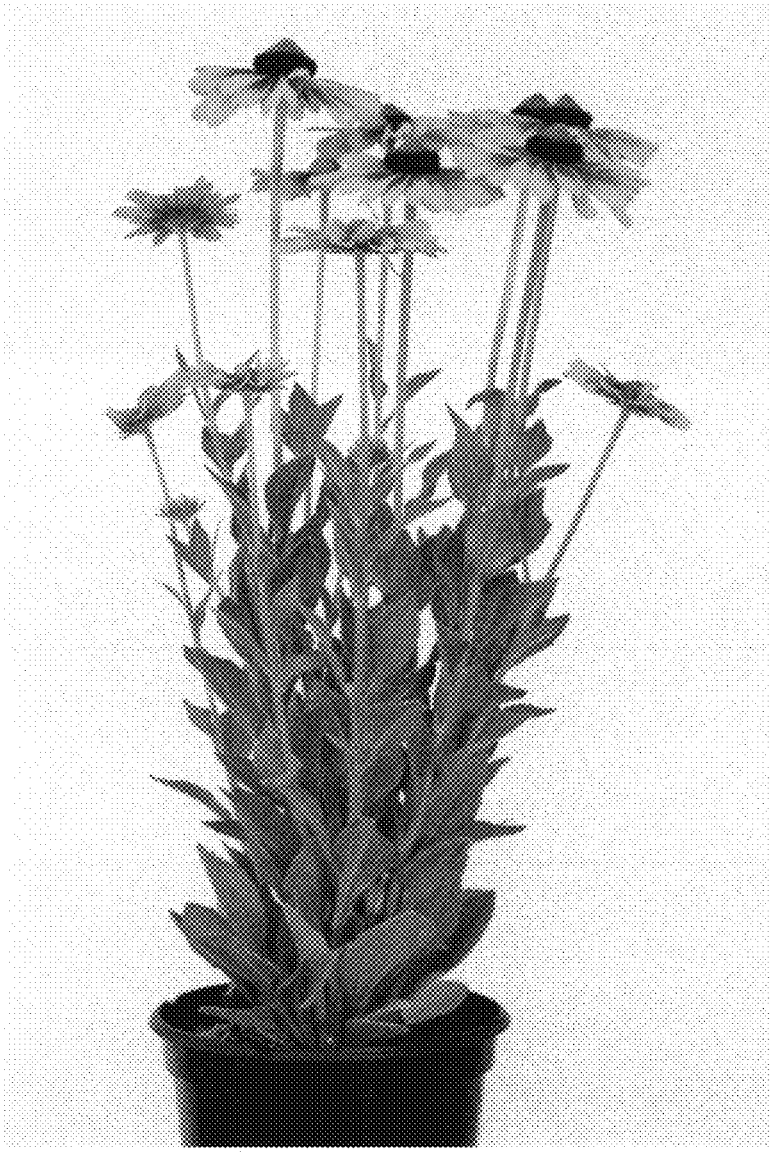
Figure 2:
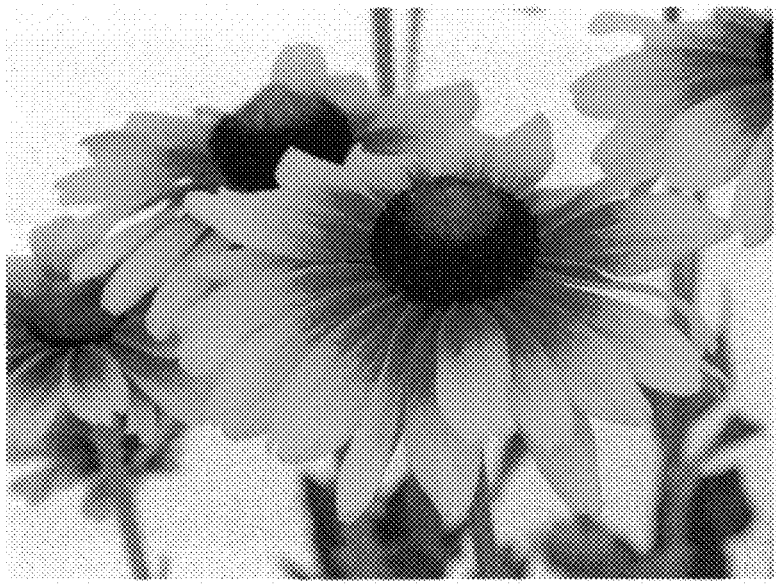

The photograph in FIG. 2 provides a close-up view of the inflorescences of 'RUDBR159'.

Figure 3:
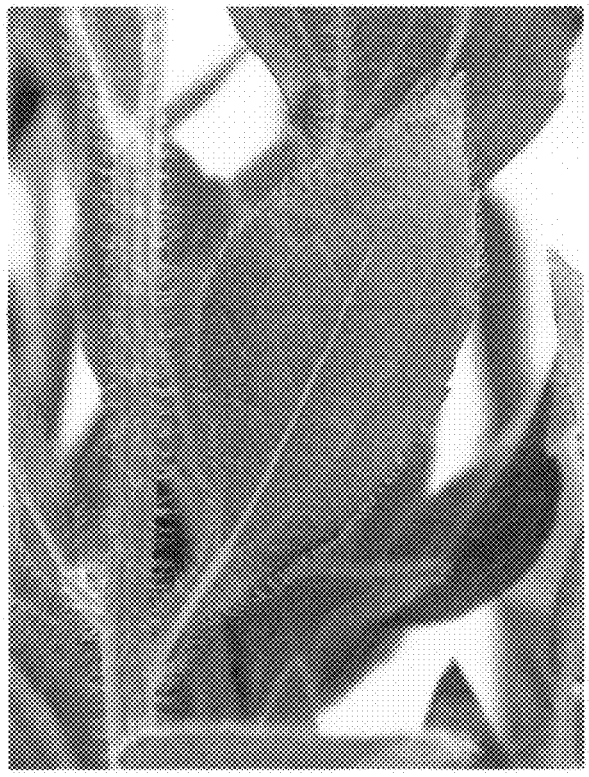

The photograph in FIG. 3 provides a close-up view of the foliage of 'RUDBR159'.

The colors in the photographs are as close as possible with the photographic and printing technology utilized and the color values cited in the detailed botanical description accurately describe the colors of the new *Rudbeckia*.

BOTANICAL DESCRIPTION OF THE PLANT

The following is a detailed description of 4-month-old plants of 'RUDBR159' as grown outdoors in 19-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Average of 13 weeks from early summer to late summer in the Netherlands.

*Plant type*.—Perennial.

*Plant habit*.—Upright, compact.

*Plant shape*.—Narrow obovate.

*Height and spread*.—Average of 40.5 cm in height from soil level to top of foliar plane and 58.7 cm in height from soil level to top of floral plane, 34 cm in diameter.

*Hardiness*.—At least in U.S.D.A. Zones 4 to 10.

*Diseases and pests*.—No susceptibility and resistance to diseases or pests has been observed.

*Root description*.—Fine and fibrous.

*Propagation*.—Tissue culture.

*Root development*.—An average of 3 weeks for root initiation with a young rooted plant produced in an average of 6 weeks.

*Growth rate and vigor*.—Vigorous.

Stem description:

*Shape*.—Moderately angled.

*Stem color*.—Young stems; 144B to 144C, mature stems; 144B, 143B at the angles.

*Stem size*.—An average of 5 mm in diameter and an average of 31.3 cm in height.

*Stem surface*.—Moderately glossy and densely covered with strigose hairs; an average of 2 mm in length and close to NN155D in color.

*Stem number*.—Average of 11 main stem and 1 lateral branch per main stem.

*Internode length*.—An average of 3.3 cm in length.

*Stem aspect*.—Main stems; average of 10° to vertical, lateral branches; average of 17.5° to main stems.

*Branching*.—Freely branching from base with lateral stems.

Foliage description:

*Leaf shape*.—Elliptic to ovate.

*Leaf division*.—Simple.

*Leaf base*.—Cuneate.

*Leaf apex*.—Acute.

*Leaf venation*.—Pinnate, color upper surface 147D, color lower surface 146D.

*Leaf margins*.—Coarsely serrate, slightly undulate.

*Leaf attachment*.—Petiolate.

*Leaf arrangement*.—Alternate.

*Leaf size*.—Average of 7.6 cm in length and 4.1 cm in width.

*Leaf color*.—Young upper surface; 137B, young lower surface; 138A, mature upper surface; 137A, mature lower surface; a color between 147D.

*Leaf surface*.—Upper surface matte, and non-rugose, rough to touch, lower surface is matte, slightly rugose, rough to touch, both surfaces densely pubescent with short strigose hairs; an average of 1.75 mm in length and N155D in color.

*Petioles*.—Average of 3.6 cm in length, flattened, average diameter at widest point 7 mm and at narrowest point 3 mm, upper surface color; 147D with margins 137A, lower surface color; 145A to 145B with margins 137B, both surfaces slightly glossy and densely covered with strigose hairs; am average of 1.75 mm in length and N155D in color.

Flower description:

*Type*.—Terminal capitulum, consisting of ray florets and Disk florets.

*Capitulum number*.—1 per stem, up to 16 per plant.

*Lastingness of inflorescence*.—Average of 2 weeks, persistent.

*Capitulum size*.—Matures to about 4 cm in height and 11.3 cm in diameter, disk size is an average of 3.4 cm in diameter.

*Fragrance*.—None.

*Involucral bracts* (*phyllaries*).—Broadly cuneate base, acute apex, narrow oblong in shape, entire margins, average of 34 arranged in two rows, 1.7 cm in length and 2 mm in width, color; upper surface when fully open 143A, lower surface when fully open 138B, both surfaces matt and densely covered with strigose hairs; an average of 1.5 mm in length and NN155D in color.

*Receptacle*.—Broadly ovate in shape, an average of 1.5 cm in height and diameter, 157B in color.

*Bracts*.—1 at each Disk floret, spirally placed on Disk, soft, flattened, an average of 1.7 cm in length and 1 mm in diameter, narrow oblong in shape, acute apex, broadly cuneate in shape, color; upper surface 143A, lower surface 138B, matte surface and moderately pubescent with hairs; an average of 1.5 mm in length and NN155D in color.

*Buds*.—Globular in shape, immature ray florets pointed upward and curling inward, average of 2 cm in length and up to 3.1 cm in diameter, immature ray florets are 154B in color, immature involucral bracts upper surface 143A, lower surface 138B, surface of bracts and immature ray florets densely covered with strigose hairs; an average of 2 mm in length and 155A in color, with hairs adpressed on immature ray florets.

*Peduncle*.—Strong, straight on top of main flowering stem, average of 18.5 cm in length and 4.5 mm in diameter, color; 144B and axially striped 143B, surface slightly glossy sand densely covered with short strigose hairs; an average of 2 mm in length and NN155D in color.

*Ray florets*.—Average of 23 (varying between 20 and 24), rotate around the disk, oblong in shape, average of 5.2 cm in length and 1.8 cm in width, praemorse apex, cuneate base, entire margin, both surfaces are velvety, matte and glabrous, held near horizontal, color; when opening upper surface 17B, fading towards the base to N172A and 175B, when opening lower surface 14B, fading towards the base to 153D, when fully open upper surface and veins 17A, fading towards the base to 175B and 178A, when fully open lower surface 14A, fading to 15A at the base, veins 146D.

*Disk flowers*.—Average about 1,000, slightly curved and tubular in shape, arranged spirally on a conical receptacle, lower 90% fused into tube, upper 10% free, about 7 mm in length and 2 mm in width, free lobes have entire margins, both surfaces glabrous and moderately glossy, color; when opening and fully open upper and lower surface 200A, mid-section 155C, slightly tinged N187D, base 155A.

Reproductive organs:

*Gynoecium*.—Pistil; 1,7 mm in length, style; 5 mm in length, color; 200A, mid-section 155C and tinged 187C with base 155C, stigma; cleft, decurrent, 5 mm in diameter, 200A in color, ovary; 155A in color.

*Androecium*.—Stamens; 5, filaments; 2 mm in length, 160D in color, anther; narrow oblong in shape, 3 mm in length, 0.5 mm in width, 200C and 200D in color, Pollen; low in quantity and 15A in color.

*Fruit/seed*.—None observed.

It is claimed:

1. A new and distinct cultivar of *Rudbeckia* plant named 'RUDBR159' substantially as herein illustrated and described.

* * * * *